(12) United States Patent
Steynberg

(10) Patent No.: US 7,612,118 B2
(45) Date of Patent: Nov. 3, 2009

(54) METHOD OF QUENCHING A SLURRY

(75) Inventor: André Peter Steynberg, Gauteng Province (ZA)

(73) Assignee: SASOL Technology (Proprietary) Limited, Gauteng Province (ZA)

( * ) Notice: Subject to any disclaimer, the term of this patent is extended or adjusted under 35 U.S.C. 154(b) by 459 days.

(21) Appl. No.: 11/501,995

(22) Filed: Aug. 10, 2006

(65) Prior Publication Data

US 2006/0272986 A1   Dec. 7, 2006

Related U.S. Application Data

(62) Division of application No. 10/308,772, filed on Dec. 3, 2002, now abandoned.

(30) Foreign Application Priority Data

Dec. 4, 2001   (ZA) ................................ 2001/9976

(51) Int. Cl.
*C07C 27/00* (2006.01)

(52) U.S. Cl. ...................................... 518/700; 518/728
(58) Field of Classification Search ................. 518/700, 518/728
See application file for complete search history.

(56) References Cited

U.S. PATENT DOCUMENTS

| | | | | |
|---|---|---|---|---|
| 4,113,602 A | * | 9/1978 | Gorbaty et al. | ................ 201/24 |
| 6,278,034 B1 | * | 8/2001 | Espinoza et al. | ............ 585/275 |

\* cited by examiner

*Primary Examiner*—Jafar Parsa
(74) *Attorney, Agent, or Firm*—Marshall, Gerstein & Borun LLP

(57) ABSTRACT

A method is provided for quenching a slurry in a slurry vessel of slurry phase apparatus which comprises a gas distributor arranged to inject a gas into the slurry at a predetermined level, and an apertured solid particles support below the level at which the gas distributor is disposed to inject the gas. The method includes introducing a quenching liquid into the slurry vessel below the apertured support and passing the quenching liquid into the slurry through the apertures of the apertured support.

5 Claims, 2 Drawing Sheets

METHOD OF QUENCHING A SLURRY

This is a divisional of U.S. patent application Ser. No. 10/308,772, filed Dec. 3, 2002, the entire disclosure of which is incorporated herein by reference.

THIS INVENTION relates to slurry phase apparatus.

There are many applications in the chemical process industry in which a gas is injected into a slurry which comprises particular solids suspended in a liquid. Typically, a gas distributor is used to inject gas into the slurry. A commonly used gas distributor comprises an apertured sparger pipe or device for uniformly distributing the gas into the slurry.

Problems associated with the use of a sparger device such as a sparger pipe include plugging of the apertures or gas injectors of the sparger pipe, backflow of slurry into and through the sparger pipe in the event of an interruption in the flow of gas and settling of the particular solids in stagnant zones. A characteristic of many slurries is that once the particular solids, e.g. catalysts, have settled out of the liquid phase it is difficult to resuspend the solids in the liquid phase. In many slurry phase reaction applications, settled solid catalysts will also be problematic due to resulting poor heat transfer causing hot and cold temperature spots inside the slurry that may be dangerous or detrimental to the reaction or reactions taking place or to the particular solid catalysts employed.

It is an object of the present invention to provide slurry phase or suspension apparatus which at least alleviates the abovementioned problems associated with the use of a sparger device, particularly when an interruption of the gas flow to the sparger device is experienced. It is also an object of the present invention to provide improved methods of quenching a slurry and of dealing with the results of slurry backflow into a sparger device.

According to one aspect of the invention, there is provided slurry phase apparatus which includes a slurry vessel for holding a slurry comprising a liquid and solid particles and gas distribution means for injecting a gas into the slurry, the gas distribution means including a sparger device which includes an apertured sparger portion inside the slurry vessel, an inlet portion leading into the slurry vessel and an outlet portion leading from the slurry vessel; and closure means, external of the slurry vessel, operable to allow or deny flow from the sparger portion out through the outlet portion of the sparger device.

The inlet portion of the sparger device may enter the slurry vessel at an elevation which is the same as, or above, the elevation at which the sparger portion is located inside the slurry vessel. Preferably, the inlet portion includes a flow leg inside the slurry vessel, the flow leg being substantially vertically orientated.

The outlet portion of the sparger device may lead from the slurry vessel at an elevation which is the same as, or lower than, the elevation at which the sparger portion is located inside the slurry vessel.

The gas distribution means may include a collection vessel into which the outlet portion of the sparger device leads. Typically, the closure means includes at least one valve which is typically located between the slurry vessel and the collection vessel. However, it is to be appreciated that the closure means, when in the form of a valve or valves, may be located in a line or lines leading into and/or out of the collection vessel, thereby also allowing opening or closing of the outlet portion of the sparger pipe as desired, through the collection vessel.

The gas distribution means may include a return line leading from the collection vessel into the slurry vessel. Typically, a valve will be located in the return line between the collection vessel and the slurry vessel.

The gas distribution means may include a line or lines which can be used to pressurise or depressurise the collection vessel.

The sparger device is thus typically characterised by the vertical down orientation of a length or leg of the inlet portion inside the slurry vessel, the absence of a valve inside the slurry vessel in the inlet portion, a continuous flow path without dead spaces through the sparger portion, and the outlet portion which extends through a wall of the slurry vessel into the collection vessel, with a normally closed valve in the outlet portion of the sparger device between the slurry vessel and the collection vessel.

The sparger portion of the sparger device may include a plurality of gas injectors, which may be of any known design suitable for injecting a gas into a slurry comprising particulate solids suspended in a liquid. If desired, the gas injectors may each include a conduit through which the gas passes after exiting through the aperture or orifice in the sparger portion and prior to entering the slurry. In this way the gas velocity as the gas exits the gas injector is advantageously decreased, to inhibit solids attrition.

It will be appreciated that the sparger device may have more than one inlet portion and/or more than one outlet portion. It will also be appreciated that the apparatus of the invention may include more than one sparger device, in which case the sparger portions of the sparger devices should preferably be in more or less the same horizontal plane.

In one embodiment of the invention, the sparger portion of the sparger device is in the form of a pipe arranged in a spiral in a horizontal plane. However, it is to be appreciated that other geometries may be used for the sparger portion or sparger portions.

The gas distribution means may include a purge fluid line leading into the sparger device for purging the sparger device. Typically, the purge fluid line leads into the inlet portion of the sparger device.

The apparatus may include an apertured support for supporting settled solid particles, the apertured support being located inside the slurry vessel below the sparger portion of the sparger device; and a fluid inlet for introducing a fluid into the slurry vessel below the apertured support.

Typically, the apertures of the apertured support are small enough in use to prevent at least 90% by mass, preferably at least 96% by mass, e.g. about 98% by mass of the solid particles in the slurry from passing therethrough.

In use, a fluid, typically a liquid, may be fed by means of the fluid inlet into the slurry vessel below the apertured support, and passed upwardly through the apertures, to assist with particulate solids suspension, particularly when gas flow through the sparger device is first introduced or reintroduced following interruption of gas flow, and/or as a quench fluid.

Preferably, at least some of the orifices or apertures of the sparger portion, or at least some of the gas injectors, when present, are orientated towards the apertured support, in use to ensure that the slurry is sufficiently agitated to avoid the settling of solids onto the apertured support below the sparger portion. Preferably, each gas injector, when present, and each aperture or orifice in the sparger portion is free draining.

The apertured support may include a plurality of parallel spaced rows or strips of wedge wire which between them define the apertures. The wedge wire strips may be supported on a plurality of spaced bonding strips.

The slurry phase apparatus may include a quench fluid sparger, in addition to the apertured support and fluid inlet, and may also include cooling medium conduits. The quench fluid sparger may be located above the portion of the sparger device which is located inside the slurry vessel. Typically, when cooling medium conduits, such as boiler circulation water conduits, are present, the quench fluid sparger is located below the cooling medium conduits. Although the quench fluid sparger may be a gas sparger, it will typically be a liquid sparger for sparging a quench liquid into the slurry.

According to another aspect of the invention, there is provided slurry phase apparatus which includes a slurry vessel for holding a slurry comprising a liquid and solid particles;

gas distribution means which includes a sparger device, a portion of which extends slurry vessel for injecting a gas into the slurry;

an apertured support below the portion of the sparger device inside the slurry vessel for supporting settled solid particles; and a fluid inlet for introducing a fluid into the slurry vessel below the apertured support.

The gas distribution means and the apertured support may be as hereinbefore described.

The invention extends to the use of slurry phase apparatus as hereinbefore described in a process in which a gas is injected into a slurry which includes particulate solids suspended in a liquid.

The process may be selected from the group consisting of coal liquefaction, methanol synthesis, higher alcohol synthesis, hydrogenation processes, and hydrocarbon synthesis from carbon monoxide and hydrogen. In one particular embodiment of the invention, the process is a Fischer-Tropsch process for hydrocarbon synthesis from carbon monoxide and hydrogen.

According to a further aspect of the invention, there is provided a method of quenching a slurry in a slurry vessel of slurry phase apparatus which comprises gas distribution means arranged to inject a gas into the slurry at a predetermined level, and an apertured solid particles support below the level at which the gas distribution means is arranged to inject the gas, the method including introducing a quenching fluid into the slurry vessel below the apertured support and passing the quenching fluid into the slurry through the apertures of the apertured support.

Typically, the quenching fluid is a liquid at a temperature which is lower than the temperature of the, slurry in the slurry vessel, and the slurry vessel is typically being used for holding a slurry in which an exothermic reaction takes place.

According to yet another aspect of the invention, there is provided a method of introducing or reintroducing a gas into a slurry vessel of slurry phase apparatus as hereinbefore described, the method including operating the closure means to allow flow through the outlet portion of the sparger device;

flushing the sparger device out through the outlet portion to remove settled material which may be present in the sparger device;

operating the closure means to deny flow through the outlet portion of the sparger device; and introducing or reintroducing the gas into the slurry vessel through the sparger device.

The method may include flushing any settled material from the sparger device into the collection vessel.

Flushing the settled material from the sparger device may include purging the sparger device with a purging fluid, which may be a liquid, a liquid followed by a gas, or a gas only.

The method may include passing a fluid upwards through the apertured support to assist with suspension of particulate solids which have settled onto the apertured support. Typically, the fluid is a liquid.

The method may include returning material flushed into the collection vessel to the slurry vessel, e.g. by pressurising the collection vessel.

The invention will now be described, by way of example, with reference to the accompanying diagrammatic drawings.

Figure 1:
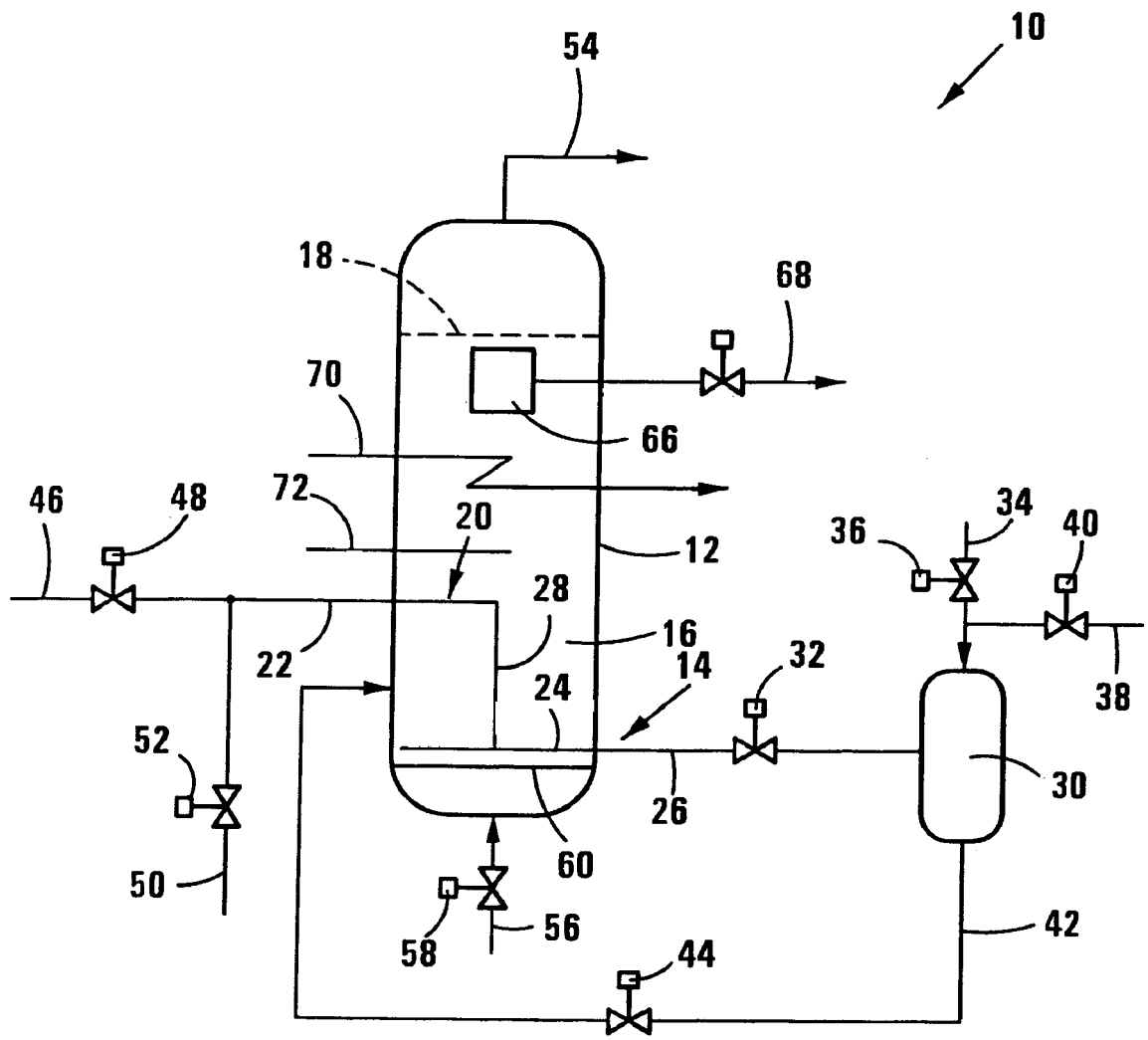
FIG. 1 shows a simplified flow diagram of slurry phase apparatus in accordance with one embodiment of the invention.

Referring to FIG. 1 of the drawings, reference numeral 10 generally indicates slurry phase or suspension apparatus in accordance with the invention. The apparatus 10 includes an upright cylindrical Fischer-Tropsch synthesis slurry phase reactor vessel 12 and gas distribution means generally indicated by reference numeral 14.

The vessel 12 provides a slurry bed zone normally containing a slurry bed 16 of catalyst particles suspended in liquid product and through which gas is passing, as described in more detail hereunder. The slurry bed 16 has an upper surface 18, and an expanded height of the slurry bed 16 while gas passes through it is typically between 10 meters and 40 meters, depending on the length of the vessel 12.

The gas distribution means 14 comprises a sparger pipe 20. The sparger pipe 20 has an inlet portion 22, a horizontal apertured sparger portion 24 and an outlet portion 26. The inlet portion 22 extends through the cylindrical wall of the reactor vessel 12 to the centre of the reactor vessel 12, whereafter it turns vertically downwardly to provide a leg 28 which is substantially vertically orientated.

Figure 2:
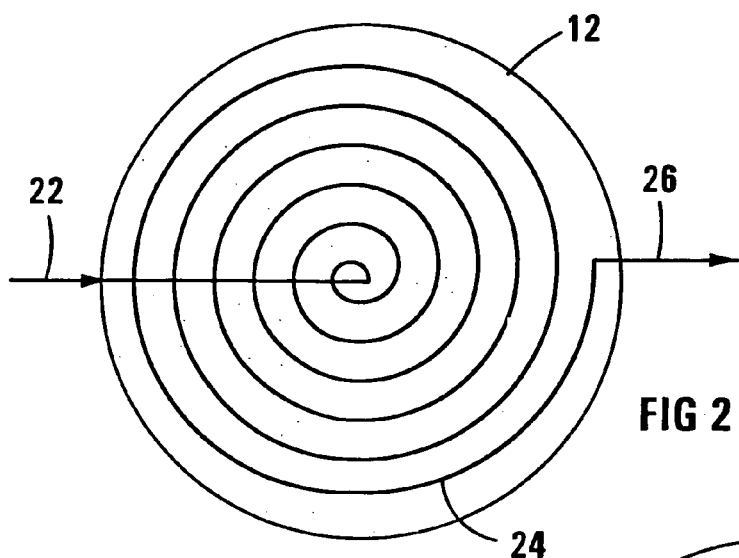
FIG. 2 shows a schematic top plan view of one embodiment of gas distribution means, which includes a sparger pipe, which extends through a slurry vessel of the apparatus of FIG. 1.

As is clearly shown in FIG. 2 of the drawings, the apertured sparger portion 24 is arranged in a spiral. As shown in FIG. 1 of the drawings, the spiral is located in a horizontal plane inside the reactor vessel 12. The inlet portion 22 of the sparger pipe 20 thus enters the reactor vessel 12 at an elevation which is above the elevation at which the sparger portion 24 is located inside the reactor vessel 12. The vertical distance between the elevation at which the inlet portion 22 enters the reactor vessel 12 and the elevation at which the spiral coil of the sparger portion 24 is located, may be any desired and practical distance.

The gas distribution means 14 further includes a collection vessel 30 into which the outlet portion 26 of the sparger pipe 20 runs. The collection vessel 30 is at more or less the same elevation as the sparger portion 24, so that the outlet portion 26 of the sparger pipe 20 leads from the reactor vessel 12 at an elevation which is the same as the elevation at which the sparger portion 24 is located, and which remains at this elevation until the outlet portion 26 opens out into the collection vessel 30. Between the vertical leg 28 of the inlet portion 22, and the collection vessel 30, there is thus a continuous flow path without any dead spaces. A normally closed valve 32 is located in the outlet portion 26 of the sparger pipe 20, between the reactor vessel 12 and the collection vessel 30.

A line 34, which can be used to pressurise the collection vessel 30, is isolated from the collection vessel 30 by means of a normally closed valve 36. A vent line 38 is isolated from the collection vessel 30 by means of a normally closed valve 40. A return line 42 leads from the collection vessel 30 back to the reactor vessel 12 and enters the reactor vessel 12 at an elevation which is above the sparger portion 24. A normally closed valve 44 is located in the return line 42 between the collection vessel 30 and the reactor vessel 12.

A synthesis gas flow line or conduit 46 is connected to the inlet portion 22 of the sparger pipe 20 via a shut-off valve 48. A purge fluid line 50 joins the inlet portion 22 of the sparger pipe 20 between the shut-off valve 48 and the reactor vessel 12. A normally closed valve 52 is located in the purge fluid line 50.

A gas withdrawal flow line or conduit 54 leads from a gas outlet (not shown) provided at the top of the reactor vessel 12. A quench liquid line 56 enters the reactor vessel 12 at the bottom of the reactor vessel 12, below the sparger portion 24. The quench liquid line 56 is provided with a normally closed valve 58.

Figure 4:
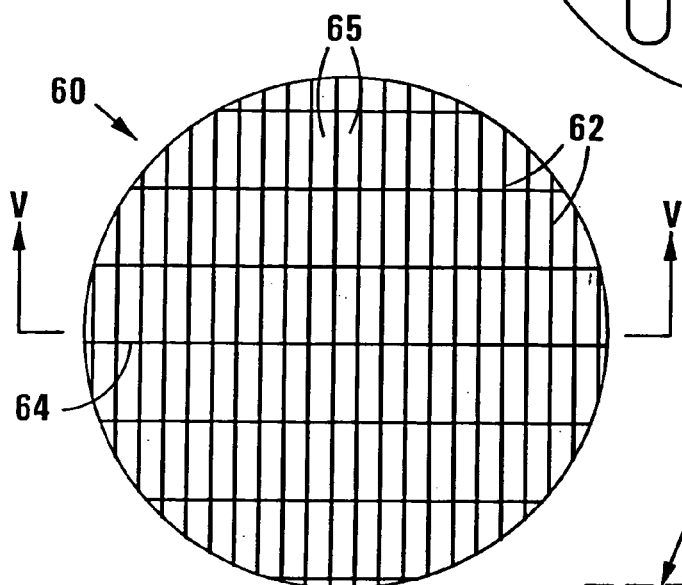
FIG. 4 shows a schematic top plan view of an apertured support located inside the slurry vessel of the apparatus of FIG. 1.
Figure 5:
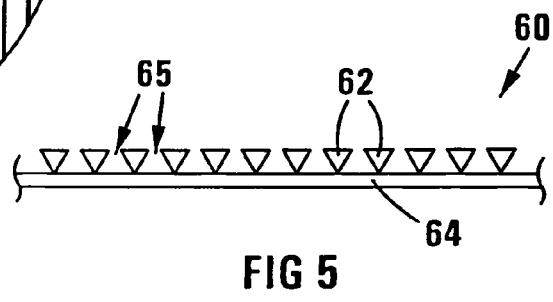
FIG. 5 shows an enlarged vertical section taken at V-V through the apertured support of FIG. 4.

An apertured support 60 for supporting settled solid catalyst particles, is located inside the reactor vessel 12 below the sparger portion 24 of the sparger pipe 20. The apertured support 60 comprises a plurality of parallel spaced rows or strips of wedge wire 62 as shown in FIGS. 4 and 5 of the drawings. The rows of wedge wire 62 are supported on a plurality of parallel spaced bonding strips 64, only some of which are shown in FIG. 4 of the drawings. Apertures 65 are thus defined between the wedge wire rows or strips 62 through which liquid may pass in an upward direction. However, the apertures are sized such that their maximum dimensions are smaller than the minimum dimensions of the solid catalyst particles in the slurry bed 16.

The apparatus 10 may also include a plurality of filter elements 66, only one of which is shown in FIG. 1 of the drawings. The filter elements 66 are connected to a liquid product withdrawal line 68 through which liquid product can be withdrawn. The filter elements 66 are typically configured and operated as disclosed in WO 00/45948, the specification of which is incorporated herein by reference. However, it is to be appreciated that any suitable solids separation arrangement for separating catalyst particles from the liquid product may be used and this arrangement may be located either inside or outside the vessel 12.

Cooling pipes, generally indicated by reference numeral 70 are provided for removing heat from the slurry bed 16 in use. Furthermore, although not shown in FIG. 1 of the drawings, the reactor vessel 12 will typically include downcomers, as also disclosed in WO 00/45948.

In use, synthesis gas, comprising mainly carbon monoxide and hydrogen, enters the sparger pipe 20 from the synthesis gas flow line 46 and is injected into the slurry bed 16 through the apertures or orifices of the sparger portion 24, in order to maintain the slurry bed 16 in the reactor vessel 12. Typically, the apertures or orifices of the sparger portion 24 are located in the bottom of the sparger portion 24, so that the sparger portion 24 is self-draining and so that gas is injected downwardly towards the apertured support 60. This assists in agitating the slurry above the apertured support 60 to a sufficient extent to inhibit the settling of solid catalyst particles onto the apertured support during normal operation of the apparatus 10. If desired, any suitable kind of gas injector can be used in conjunction with the apertures or orifices in the sparger pipe, to reduce the gas velocity before the gas enters the slurry bed 16, thereby to inhibit solids attrition. However, it is to be appreciated that it is an advantage of the apparatus 10, as illustrated, that gas injectors with barriers or valve arrangements are not required.

The slurry bed 16 comprises the catalyst particles suspended in liquid product, i.e. liquid wax produced in the reactor vessel 12 on the action of the gaseous reactants. The catalyst particles are maintained in suspended state in the slurry bed 16 by means of the turbulence created therein by the gas passing upwardly therethrough.

The reactor vessel 12 is typically maintained at an operating pressure of between about 10 bar and about 40 bar, more typically between about 20 bar and about 30 bar, and at an operating temperature of between 180.degree. C. and 280.degree. C., typically about 220.degree. C. to 260.degree. C. The operating pressure and the operating temperature selected may depend on the nature and spread of gaseous and liquid product required and the type of catalyst used. Naturally, the reactor vessel 12 is provided with suitable temperature control means, such as the cooling pipes 70 for controlling the reaction temperatures, as well as suitable pressure control means such as one or more pressure control valves (not shown).

In the reactor vessel 12, as the synthesis gas passes through the slurry bed 16, the carbon monoxide and hydrogen react to form a range of products in accordance with known Fischer-Tropsch reactions. Some of these products are in gaseous form at the operating conditions of the vessel 12 and are withdrawn, together with unreacted synthesis gas, along the flow line 54. Some of the products produced, such as the wax already mentioned, are in liquid form at the operating conditions of the reactor vessel 12, and act as the suspension medium for the catalyst particles. As liquid product is formed, the level 18 of the slurry bed 16 naturally rises, and the liquid product is thus withdrawn, by means of the filter elements 66 and the liquid product withdrawal line 68 to maintain the slurry bed level.

When gas flow through the sparger pipe 20 is interrupted for any reason, the slurry bed 16 slumps and a number of potentially problematic events occur.

The catalyst particles settle on the apertured support 60 and once settled, it may be very difficult to resuspend the settled particles in the liquid phase. The settled solid catalyst will continue to catalyse reactions at the bottom of the reactor vessel 12 but, as slurry circulation into upper regions of the reactor vessel 12, where heat removal by means of the cooling pipes 70 is done, no longer takes place, high temperatures which may damage the solid catalyst are experienced at the bottom of the reactor vessel 12 when the synthesis gas flow is interrupted. This unwanted effect is enhanced by the fact that no cooling occurs as the result of colder synthesis gas entering the reactor vessel 12. Lastly, problems may be encountered due to the backflow of slurry into and through the sparger pipe 20 in the event of an interruption of the synthesis gas flow. Some of these problems only manifest upon the reintroduction of the synthesis gas flow to the sparger pipe 20, such as plugging of the apertures or orifices of the sparger portion 24 from the upstream side thereof upon reintroduction of the synthesis gas flow.

The present invention provides a simple and effective solution to the abovementioned problems, avoiding the need for any moving parts, such as barrier or valve type arrangements for gas injectors. The apparatus 10 of the invention also does not require the use of a valve in the inlet to the sparger pipe 20 inside the reactor vessel 12 to prevent the backflow of slurry into the sparger pipe 20 in the event that the synthesis gas flow is interrupted.

In the event of slurry backflow into the sparger portion 24 as a result of an interruption in the synthesis gas flow, the slurry can be cleared easily from the sparger pipe 20 prior to re-establishing normal operating conditions, i.e. prior to reestablishing synthesis gas flow. The slurry is removed from the sparger pipe 20 by establishing a lower pressure in the collection vessel 30, e.g. by opening the valve 40 so that the collection vessel 30 loses pressure to atmosphere, typically through a flare. Thereafter, the valve 32 between the collection vessel 30 and the sparger portion 24 is opened to flush slurry and any settled solids from the sparger pipe 20 into the collection vessel 30. As a result of the design of the inlet portion 22 of the sparger pipe 20, and in particular the presence of the vertical leg 28, there may be sufficient liquid inside the sparger pipe 20 to flush the settled solids into the collection vessel 30. However, if required, a purge fluid, typically a liquid or a liquid followed by a gas, but in some cases a gas only, is introduced through the purge fluid line 50, with the shut-off valve 48 being closed. The purge fluid is then used to assist with the sweep of the settled solids from the sparger pipe 20 into the collection vessel 30. Naturally, the pressure inside the sparger pipe 20 must be kept higher than the pressure inside the reactor vessel 12 during the flushing operation, to prevent further ingress of slurry into the sparger pipe 20. As a result, some of the liquid and solids may flow out of the sparger pipe 20 via the apertures or orifices, and the gas injectors, if present, into the slurry bed 16.

In order to take care of the problems of settled solids on the apertured support 60, and high temperatures in the bottom region of the reactor vessel 12 when the synthesis gas flow to the sparger pipe 20 is interrupted, a quench liquid is passed through the quench liquid line 56 into the reactor vessel 12, below the apertured support 60, after the valve 58 has been opened. The quench liquid may be liquid product at a temperature lower than the temperature of the slurry bed 16. Liquid is passed through the apertures 65 in the apertured support 60 in an upward direction to quench reactions taking place in the bottom region of the reactor vessel 12 catalysed by the settled solid catalyst. As will be appreciated, this liquid flow can also advantageously be used to assist with the suspension or resuspension of catalyst particles when the synthesis gas flow is first introduced or is reintroduced into the reactor vessel 12 through the sparger pipe 20. It will also be appreciated that the line 56 and the apertured support 60 can be used intermittently during normal operation of the apparatus 10, to resuspend catalyst particles settling into stagnant zones on the apertured support 60.

Although not shown in the drawings, the apparatus 10 includes a further, quench liquid sparger above the sparger portion 24 but below the cooling pipes 70. Thus, when synthesis gas flow through the sparger pipe 20 is interrupted, the quench liquid is also fed into the slurry bed 16 by means of the quench liquid sparger, advantageously assisting in preventing temperatures inside the slurry bed 16, below the cooling pipes 70, from becoming too high. Simultaneously, recycle gas may be fed into the sparger pipe 20 in an attempt to keep the sparger pipe 20 open.

Figure 3:
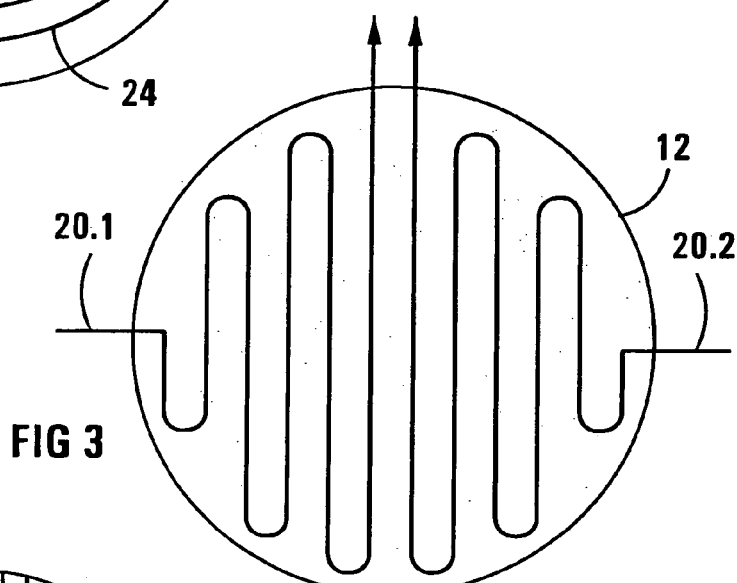
FIG. 3 shows a schematic top plan view of two sparger pipes extending through a slurry vessel in accordance with another embodiment of the gas distribution means.

Referring to FIG. 3 of the drawings, gas distribution means comprising two sparger pipes 20.1 and 20.2 is shown. The sparger pipes 20.1 and 20.2 thus each has an inlet portion, a horizontal apertured sparger portion and an outlet portion. As with the sparger pipe 20, the sparger pipes 20.1 and 20.2 each has a vertical leg (not shown in FIG. 3) typically forming part of the inlet portion, with the inlet portion extending through the cylindrical wall of the reactor vessel 12 at an elevation which is above the elevation of the sparger portions inside the reactor vessel 12.

As illustrated in FIG. 3 of the drawings, instead of using a single sparger pipe 20, two or more sparger pipes, such as the sparger pipes 20.1 and 20.2, can be used to maintain the slurry bed 16 in the reactor vessel 12. As will be appreciated, each sparger pipe 20.1 and 20.2 may be connected to its own collection vessel and purge line, or, instead, a common collection vessel and a common purge line may be used.

What is claimed is:

1. A method of quenching a slurry of solid catalyst particles suspended in a liquid in a slurry vessel of slurry phase apparatus which comprises a gas distributor arranged to inject a gas into the slurry at a predetermined level, and an apertured solid particles support below the level at which the gas distributor is disposed to inject the gas, during interruption of gas flow through the gas distributor, the method including introducing a quenching liquid into the slurry vessel below the apertured support and passing the quenching liquid into the slurry through the apertures of the apertured support, thereby to quench exothermic reactions taking place in a bottom region of the slurry vessel catalysed by solid catalyst settled on the apertured solid particles support and to assist with re-suspension of catalyst particles.

2. The method as claimed in claim 1, wherein the slurry vessel is used in a process selected from the group consisting of coal liquification, methanol synthesis, higher alcohol synthesis, a hydrogenation process, and hydrocarbon synthesis from carbon monoxide and hydrogen.

3. The method as claimed in claim 1, wherein the quenching liquid is at a temperature which is lower than the temperature of the slurry in the slurry vessel.

4. The method as claimed in claim 1, which includes the step of introducing a quench fluid into the slurry vessel at a level above the predetermined level at which gas is injected into the slurry.

5. The method as claimed in claim 4, wherein the quench fluid is a liquid at a temperature which is lower than the temperature of the slurry in the slurry vessel, and wherein the quench liquid is introduced through a liquid sparger.

* * * * *